(12) United States Patent
Braga et al.

(10) Patent No.: US 8,246,591 B2
(45) Date of Patent: Aug. 21, 2012

(54) FLANGED CONNECTOR FOR WOUND THERAPY

(75) Inventors: Richard M. Braga, North Easton, MA (US); Malcolm G. Bock, Medfield, MA (US); Kristin L. Watson, North Attleboro, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 564 days.

(21) Appl. No.: 12/358,397

(22) Filed: Jan. 23, 2009

(65) Prior Publication Data

US 2010/0191197 A1     Jul. 29, 2010

(51) Int. Cl.
*A61M 1/00*    (2006.01)

(52) U.S. Cl. ........ 604/313; 604/187; 604/192; 604/268; 604/296; 604/300; 604/304; 604/311; 604/312; 604/315; 604/316; 604/35; 604/36; 604/119

(58) Field of Classification Search ............ 604/311, 604/312, 313, 315, 316
See application file for complete search history.

(56) References Cited

U.S. PATENT DOCUMENTS

| | | | |
|---|---|---|---|
| 3,367,332 A | 2/1968 | Groves | |
| 3,486,504 A | 12/1969 | Austin, Jr. | |
| 3,572,340 A | 3/1971 | Lloyd et al. | |
| 3,712,298 A | 1/1973 | Snowdon et al. | |
| 3,809,086 A | 5/1974 | Schachet et al. | |
| 3,874,387 A | 4/1975 | Barbieri | |
| 4,080,970 A | 3/1978 | Miller | |
| 4,112,947 A | 9/1978 | Nehring | |
| 4,112,949 A | 9/1978 | Rosenthal et al. | |
| 4,136,696 A | 1/1979 | Nehring | |
| 4,266,545 A | 5/1981 | Moss | |
| 4,382,441 A | 5/1983 | Svedman | |
| 4,524,064 A | 6/1985 | Nambu | |
| 4,743,232 A | 5/1988 | Kruger | |
| 4,969,880 A | 11/1990 | Zamierowski | |
| 4,990,137 A | 2/1991 | Graham | |
| 4,997,438 A | 3/1991 | Nipper | |
| 5,071,409 A | 12/1991 | Rosenberg | |
| 5,100,395 A | 3/1992 | Rosenberg | |
| 5,100,396 A | 3/1992 | Zamierowski | |
| 5,106,629 A | 4/1992 | Cartmell et al. | |

(Continued)

FOREIGN PATENT DOCUMENTS

DE    41 11 122 A1    4/1993

(Continued)

OTHER PUBLICATIONS

Meyer, M.D., et al., "In Surgery, Medicine and the Specialties a Manual of its Practical Application", Bier's Hyperemic Treatment, Second Revised Edition, W.B. Saunders Company, 1909.

(Continued)

*Primary Examiner* — Tatyana Zalukaeva
*Assistant Examiner* — Ilya Treyger
(74) *Attorney, Agent, or Firm* — Elias Domingo

(57) ABSTRACT

A wound dressing for use in negative wound pressure therapy includes a cover layer for positioning over a wound to define a reservoir over the wound in which a reduced pressure may be maintained. At least one vacuum port is affixed to the cover layer and includes a conduit receiving portion configured to receive a fluid conduit to provide fluid communication between the fluid conduit and the reservoir. The at least one vacuum port is configured to receive the fluid conduit from a plurality of directions relative to the cover layer.

16 Claims, 6 Drawing Sheets

U.S. PATENT DOCUMENTS

| | | | |
|---|---|---|---|
| 5,141,503 | A | 8/1992 | Sewell, Jr. |
| 5,149,331 | A | 9/1992 | Ferdman et al. |
| 5,152,757 | A | 10/1992 | Eriksson |
| 5,160,322 | A | 11/1992 | Scheremet et al. |
| 5,176,663 | A | 1/1993 | Svedman et al. |
| 5,178,157 | A | 1/1993 | Fanlo |
| 5,195,977 | A | 3/1993 | Pollitt |
| 5,261,893 | A | 11/1993 | Zamierowski |
| 5,263,922 | A | 11/1993 | Sova et al. |
| D364,679 | S | 11/1995 | Heaton et al. |
| 5,484,427 | A | 1/1996 | Gibbons |
| 5,527,293 | A | 6/1996 | Zamierowski |
| 5,536,233 | A | 7/1996 | Khouri |
| 5,549,584 | A | 8/1996 | Gross |
| 5,588,958 | A | 12/1996 | Cunningham et al. |
| 5,636,643 | A | 6/1997 | Argenta et al. |
| 5,645,081 | A | 7/1997 | Argenta et al. |
| 5,678,564 | A | 10/1997 | Lawrence et al. |
| 5,701,917 | A | 12/1997 | Khouri |
| 5,733,305 | A | 3/1998 | Fleischmann |
| 5,840,049 | A | 11/1998 | Tumey et al. |
| 5,911,222 | A | 6/1999 | Lawrence et al. |
| 5,944,703 | A | 8/1999 | Dixon et al. |
| 6,010,524 | A | 1/2000 | Fleischmann |
| 6,071,267 | A | 6/2000 | Zamierowski |
| 6,117,111 | A | 9/2000 | Fleischmann |
| 6,135,116 | A | 10/2000 | Vogel et al. |
| D434,150 | S | 11/2000 | Tumey et al. |
| 6,142,982 | A | 11/2000 | Hunt et al. |
| 6,174,306 | B1 | 1/2001 | Fleischmann |
| 6,203,563 | B1 | 3/2001 | Fernandez |
| 6,261,276 | B1 | 7/2001 | Reitsma |
| 6,325,788 | B1 | 12/2001 | McKay |
| 6,345,623 | B1 | 2/2002 | Heaton et al. |
| 6,348,423 | B1 | 2/2002 | Griffiths et al. |
| 6,398,767 | B1 | 6/2002 | Fleischmann |
| 6,406,447 | B1 | 6/2002 | Thrash et al. |
| 6,420,622 | B1 | 7/2002 | Johnston et al. |
| 6,458,109 | B1 | 10/2002 | Henley et al. |
| 6,488,643 | B1 | 12/2002 | Tumey et al. |
| 6,500,112 | B1 | 12/2002 | Khouri |
| D469,175 | S | 1/2003 | Hall et al. |
| D469,176 | S | 1/2003 | Hall et al. |
| 6,520,982 | B1 | 2/2003 | Boynton et al. |
| 6,553,998 | B2 | 4/2003 | Heaton et al. |
| D475,134 | S | 5/2003 | Randolph |
| 6,557,704 | B1 | 5/2003 | Randolph |
| D478,659 | S | 8/2003 | Hall et al. |
| 6,607,495 | B1 | 8/2003 | Skalak et al. |
| 6,626,891 | B2 | 9/2003 | Ohmstede |
| 6,648,862 | B2 | 11/2003 | Watson |
| 6,685,681 | B2 | 2/2004 | Lockwood et al. |
| 6,695,823 | B1 | 2/2004 | Lina et al. |
| 6,695,824 | B2 | 2/2004 | Howard et al. |
| D488,558 | S | 4/2004 | Hall |
| 6,752,794 | B2 | 6/2004 | Lockwood et al. |
| 6,755,807 | B2 | 6/2004 | Risk, Jr. et al. |
| 6,764,462 | B2 | 7/2004 | Risk, Jr. et al. |
| 6,767,334 | B1 | 7/2004 | Randolph |
| 6,800,074 | B2 | 10/2004 | Henley et al. |
| 6,814,079 | B2 | 11/2004 | Heaton et al. |
| 6,824,533 | B2 | 11/2004 | Risk, Jr. et al. |
| 6,855,135 | B2 | 2/2005 | Lockwood et al. |
| 6,856,821 | B2 | 2/2005 | Johnson |
| 6,887,228 | B2 | 5/2005 | McKay |
| 6,887,263 | B2 | 5/2005 | Bleam et al. |
| 6,936,037 | B2 | 8/2005 | Bubb et al. |
| 6,942,633 | B2 | 9/2005 | Odland |
| 6,942,634 | B2 | 9/2005 | Odland |
| 6,951,553 | B2 | 10/2005 | Bubb et al. |
| 6,960,181 | B2 | 11/2005 | Stevens |
| 6,979,324 | B2 | 12/2005 | Bybordi et al. |
| 6,994,702 | B1 | 2/2006 | Johnson |
| 7,022,113 | B2 | 4/2006 | Lockwood et al. |
| 7,037,254 | B2 | 5/2006 | O'Connor et al. |
| 7,052,167 | B2 | 5/2006 | Vanderschuit |
| 7,070,584 | B2 | 7/2006 | Johnson et al. |
| 7,077,832 | B2 | 7/2006 | Fleischmann |
| 7,108,683 | B2 | 9/2006 | Zamierowski |
| 7,117,869 | B2 | 10/2006 | Heaton et al. |
| 7,128,719 | B2 | 10/2006 | Rosenberg |
| 7,128,735 | B2 | 10/2006 | Weston |
| 7,144,390 | B1 | 12/2006 | Hannigan et al. |
| 7,169,151 | B1 | 1/2007 | Lytinas |
| 7,182,758 | B2 | 2/2007 | McCraw |
| 7,195,624 | B2 | 3/2007 | Lockwood et al. |
| 7,198,046 | B1 | 4/2007 | Argenta et al. |
| 7,214,202 | B1 | 5/2007 | Vogel et al. |
| 7,216,651 | B2 | 5/2007 | Argenta et al. |
| D544,092 | S | 6/2007 | Lewis |
| 7,273,054 | B2 | 9/2007 | Heaton et al. |
| 7,276,051 | B1 | 10/2007 | Henley et al. |
| 7,279,612 | B1 | 10/2007 | Heaton et al. |
| 7,316,672 | B1 | 1/2008 | Hunt et al. |
| D565,177 | S | 3/2008 | Locke et al. |
| 7,338,482 | B2 | 3/2008 | Lockwood et al. |
| 7,351,250 | B2 | 4/2008 | Zamierowski |
| 7,361,184 | B2 | 4/2008 | Joshi |
| 7,381,211 | B2 | 6/2008 | Zamierowski |
| 7,381,859 | B2 | 6/2008 | Hunt et al. |
| 7,396,345 | B2 | 7/2008 | Knighton et al. |
| 7,410,495 | B2 | 8/2008 | Zamierowski |
| 7,413,570 | B2 | 8/2008 | Zamierowski |
| 7,413,571 | B2 | 8/2008 | Zamierowski |
| 7,422,576 | B2 | 9/2008 | Boynton et al. |
| 2001/0031943 | A1 | 10/2001 | Urie |
| 2001/0043943 | A1 | 11/2001 | Coffey |
| 2002/0016577 | A1 | 2/2002 | Ohmstede |
| 2002/0108614 | A1 | 8/2002 | Schultz |
| 2002/0143286 | A1 | 10/2002 | Tumey |
| 2002/0151836 | A1 | 10/2002 | Burden |
| 2003/0093041 | A1 | 5/2003 | Risk, Jr. et al. |
| 2003/0208149 | A1 | 11/2003 | Coffey |
| 2003/0212357 | A1 | 11/2003 | Pace |
| 2003/0212359 | A1 | 11/2003 | Butler |
| 2003/0219469 | A1 | 11/2003 | Johnson et al. |
| 2004/0006319 | A1 | 1/2004 | Lina et al. |
| 2004/0030304 | A1 | 2/2004 | Hunt et al. |
| 2004/0039415 | A1 | 2/2004 | Zamierowski |
| 2004/0064132 | A1 | 4/2004 | Boehringer et al. |
| 2004/0073151 | A1 | 4/2004 | Weston |
| 2004/0093026 | A1 | 5/2004 | Weidenhagen et al. |
| 2004/0122434 | A1 | 6/2004 | Argenta et al. |
| 2004/0193218 | A1 | 9/2004 | Butler |
| 2004/0241213 | A1 | 12/2004 | Bray |
| 2004/0243073 | A1 | 12/2004 | Lockwood et al. |
| 2005/0010153 | A1 | 1/2005 | Lockwood et al. |
| 2005/0020955 | A1 | 1/2005 | Sanders et al. |
| 2005/0070835 | A1 | 3/2005 | Joshi |
| 2005/0070858 | A1 | 3/2005 | Lockwood et al. |
| 2005/0085795 | A1 | 4/2005 | Lockwood et al. |
| 2005/0131327 | A1 | 6/2005 | Lockwood et al. |
| 2005/0177190 | A1 | 8/2005 | Zamierowski |
| 2005/0182445 | A1 | 8/2005 | Zamierowski |
| 2005/0222527 | A1 | 10/2005 | Miller et al. |
| 2005/0222544 | A1 | 10/2005 | Weston |
| 2005/0261642 | A1 | 11/2005 | Weston |
| 2005/0261643 | A1 | 11/2005 | Bybordi et al. |
| 2006/0015087 | A1 | 1/2006 | Risk et al. |
| 2006/0025727 | A1 | 2/2006 | Boehringer et al. |
| 2006/0039742 | A1 | 2/2006 | Cable, Jr. et al. |
| 2006/0041247 | A1 | 2/2006 | Petrosenko et al. |
| 2006/0079852 | A1 | 4/2006 | Bubb et al. |
| 2006/0100586 | A1 | 5/2006 | Karpowicz et al. |
| 2006/0100594 | A1 | 5/2006 | Adams et al. |
| 2006/0116620 | A1 | 6/2006 | Oyaski |
| 2007/0014837 | A1 | 1/2007 | Johnson et al. |
| 2007/0021697 | A1 | 1/2007 | Ginther et al. |
| 2007/0027414 | A1 | 2/2007 | Hoffman et al. |
| 2007/0032754 | A1 | 2/2007 | Walsh |
| 2007/0032755 | A1 | 2/2007 | Walsh |
| 2007/0032778 | A1 | 2/2007 | Heaton et al. |
| 2007/0055209 | A1 | 3/2007 | Patel et al. |
| 2007/0066946 | A1 | 3/2007 | Haggstrom et al. |
| 2007/0078366 | A1 | 4/2007 | Haggstrom et al. |
| 2007/0078432 | A1 | 4/2007 | Halseth et al. |

FOREIGN PATENT DOCUMENTS

| | | |
|---|---|---|
| DE | 295 04 378 U1 | 10/1995 |
| DE | 43 06 478 A1 | 12/2008 |
| EP | 0 020 662 B1 | 7/1984 |
| EP | 0 358 302 | 3/1990 |
| EP | 0 853 950 B1 | 10/2002 |
| GB | 1 549 756 | 3/1977 |
| GB | 2 195 255 A | 4/1988 |
| GB | 2 235 877 A | 3/1991 |
| SU | 1762940 | 1/1989 |
| WO | 80/01139 | 6/1980 |
| WO | 80/02182 | 10/1980 |
| WO | 84/01904 | 5/1984 |
| WO | 89/05133 | 6/1989 |
| WO | 90/11795 | 10/1990 |
| WO | 92/19313 | 11/1992 |
| WO | 96/05873 | 2/1996 |
| WO | 9605873 | 2/1996 |
| WO | 03057307 | 7/2003 |
| WO | 03101508 | 12/2003 |
| WO | 2005009488 | 2/2005 |

OTHER PUBLICATIONS

Jeter, Katherine F., et al., "Managing Draining Wounds and Fistulae: New and Established Methods", Chronic Wound Care, 1990, pp. 240-246.

Chariker, M. E. et al. (eds), "Effective Management of Incisional and Cutaneous Fistulae with Closed Suction Wound Drainage," Contemporary Surgery, vol. 34, Jun. 1989, pp. 59-63.

B.M. Kostiuchenok, et al., "The Vacuum Effect in the Surgical Treatment of Purulent Wounds," Russian Journal: Vestnik Khirurgii, Sep. 1986 (18-21).

Y.N. Usupov, et al., "Active Wound Drainage," Russian Journal: Vestnik Khirugii, Apr. 1987 (42-45).

Yu A. Davydov, et al., "Concepts for Clinical Biological Management of the Wound Process in the Treatment of Purulent Wounds Using Vacuum Therapy," Vestnik Khirugii, Feb. 1991, 132-135).

N.A. Bagautdinov (Kazan), "Variant of External Vacuum Aspiration in the Treatment of Purulent Diseases of Soft Tissues," UDC 616-002.36 (94-96).

Chardack, et al., "Experimental studies on Synthetic Substitutes for Skin and Their Use in the Treatment of Burns," vol. 155, No. 1 (128-136).

Gorica Zivadinovic, et al., "Vacuum Therapy in the Treatment of Peripheral Blood Vessels," Conference Papers of the 5th Timok Medical Days, Majdanpek, 1986 (161-164).

Ryosuke Fujimoro, M.D., et al., "Sponge Fixation Method for Treatment of Early Scars," From the Department of Dermatology in the Faculty Medicine, Kyoto University, vol. 42, No. 4, Oct. 1968 (323-326).

W. Fleischmann, et al., Vacuum Sealing: Indication, Technique and Results, Emr J Orthop Surg Tramatol (1995) 5:37-40.

Sherry Stoll, "Energetic Remedies—Cupping: Healing Within a Vacuum," https://www.suite101.com/article.cfm/energetic)remedies/74531, Apr. 13, 2005.

Mulder, G.D, et al., "Clinicians' Pocket Guide to Chronic Wound Repair," Wound Healing Publications Second Edition, 1991.

Yu A. Davydov, et al., "Vacuum Therapy in the Treatment of Purulent Lactation Mastitis," Russian Journal: Vesnik Khirurgii, Sep. 1986 (66-70).

Yu A. Davydov, et al., "Bacteriological and Cytological Assessment of Vacuum Therapy of Purulent Wounds", Vestnik Khirurgii, Oct. 1988 (48-52).

W. Fleischmann, "Vacuum Sealing for Treatment of Problematical Wounds", University Surgical Clinic and Polyclinic—Accident Surgery Department, WundForum Spezial—IHW 94.

Göran Sandén, M.D., et al., "Staphylococcal Wound Infection in the Pig: Part II. Innoculation, Quantification of Bacteria, and Reproducibility," Annals of Plastic Surgery, vol. 23, No. 3, Sep. 1989, (219-223).

Björn, et al., "Irrigation Treatment in Split-thickness Skin Grafting of Intractable Leg Ulcers," Scand J Plast Reconstr Surg 19: 211-213, 1985.

Paul Svedman, et al., "Staphylococcal Wound Infection in the Pig: Part I. Course," Annals of Plastic Surgery, vol. 23, No. 3, Sep. 1989 (212-218).

Paul Svedman, "A Dressing Allowing Continuous Treatment of a Biosurface," IRCS Medical Science: Biomedical Technology; Clinical Medicine; Surgery and Transplantation, 7, 221 (1979).

Paul Svedman, "Irrigation Treatment of Leg Ulcers," The Lancet, Sep. 3, 1983 (532-534).

H. Teder, et al., "Continuous Wound Irrigation in the Pig," Journal of Investigative Surgery, vol. 3 (399-407).

P. Svedman, "A Dressing System Providing Fluid Supply and Suction Drainage Used for Continuous or Intermittent Irrigation," Annals of Plastic Surgery, vol. 17, No. 2, Aug. 1986 (125-133).

Yu A. Davydov, et al., "Vacuum Therapy in treatment of Acute Purulent Diseases of Soft Tissues and Purulent Wounds," Vestnik Khirurgii, (Surgeon's Herald), MEDICINE Publishers, 1986.

International Search Report, Application No. PCT/US09/46877 dated Jul. 20, 2009.

US 6,216,701, 04/2001, Heaton et al. (withdrawn)

US 7,186,244, 03/2007, Hunt et al. (withdrawn)

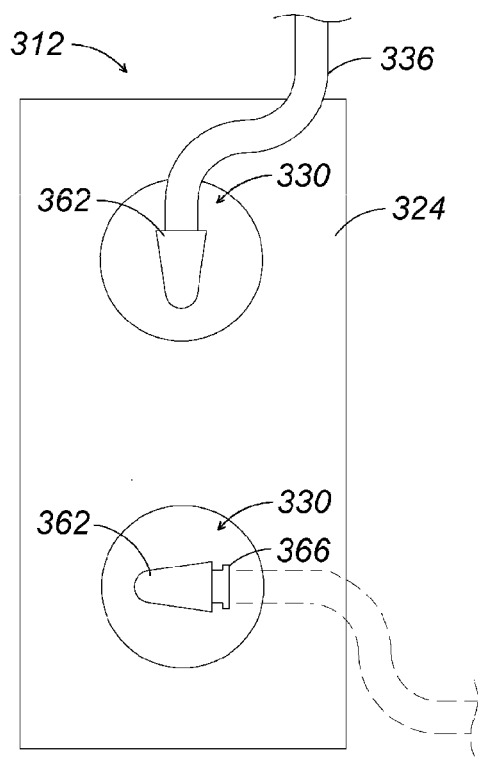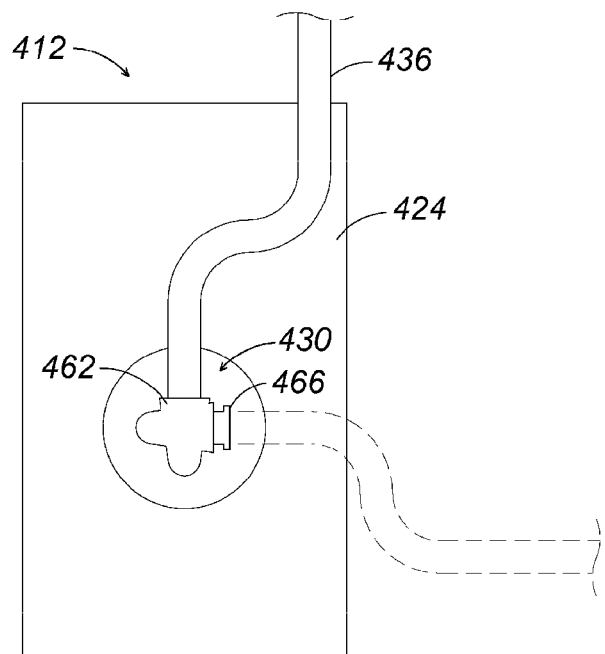
FIG. 5  FIG. 6
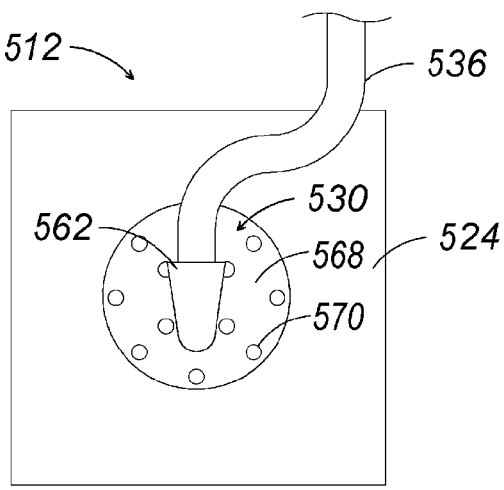
FIG. 7

FLANGED CONNECTOR FOR WOUND THERAPY

BACKGROUND

1. Technical Field

The present disclosure relates generally to treating a wound with negative or reduced pressure. In particular, the disclosure relates to a dressing having a vacuum port configured to receive a fluid conduit thereby connecting the dressing to a vacuum source.

2. Background of Related Art

Various techniques to promote healing of a wound involve providing suction to the wound. For example, a vacuum source may serve to carry wound exudates away from the wound, which may otherwise harbor bacteria that inhibit the body's natural healing process. One technique for promoting the natural healing process may be described as negative wound pressure therapy (NWPT). This technique involves the application of a reduced pressure, e.g. sub-atmospheric, to a localized reservoir over a wound. Sub-atmospheric pressure has been found to assist in closing the wound by promoting blood flow to the area, which stimulates the formation of granulation tissue and the migration of healthy tissue over the wound. This technique has proven effective for chronic or non-healing wounds, but has also been used for other purposes such as post-operative wound care.

The general NWPT protocol provides for covering the wound with a flexible cover layer such as a polymeric film, for example, to establish a vacuum reservoir over the wound where a reduced pressure may be applied by individual or cyclic evacuation procedures. To allow the reduced pressure to be maintained over time, the cover layer may include an adhesive periphery that forms a substantially fluid tight seal with the healthy skin surrounding the wound.

Although some procedures may employ a micro-pump contained within the vacuum reservoir, most NWPT treatments apply a reduced pressure using an external vacuum source. Thus, fluid communication between the vacuum source and the reservoir must be established. To this end, a cover layer will often be coupled to a vacuum port to which a fluid conduit extending from an external vacuum source may be connected. Once connected, the fluid conduit may extend from the vacuum port in an awkward direction that compromises patient movement or comfort. Accordingly, a need exists for a wound dressing for receiving a fluid conduit from a plurality of directions.

SUMMARY

The present disclosure describes a wound dressing for use in a negative wound pressure therapy treatment. The wound dressing includes a cover layer for positioning over a wound to define a reservoir over the wound in which a reduced pressure may be maintained. At least one vacuum port is affixed to the cover layer and includes a conduit receiving portion configured to receive a fluid conduit to provide fluid communication between the fluid conduit and the reservoir. The at least one vacuum port is configured to receive the fluid conduit from a plurality of directions relative to the cover layer.

The at least one vacuum port may include a base configured to remain stationary relative to the cover layer and a conduit receiving portion adapted for rotational movement relative to the stationary base. The at least one vacuum port may include an orientation fixation structure configured to lock the conduit receiving portion in position relative to the stationary base in a releasable manner. The orientation fixation structure may include a pawl on one of the stationary base and the conduit receiving portion configured to interface with a series of spaced ridges or detents on the other of the stationary base and the conduit receiving portion in a ratchet-like manner. Alternatively, the orientation fixation structure may include a plurality or radially spaced projections extending from the stationary base radially beyond the conduit receiving portion so as to define a plurality of radially spaced slots therebetween. The slots may be configured to receive the fluid conduit.

The at least one vacuum port may also include a plurality of vacuum ports. Each of the plurality of vacuum ports may have a conduit receiving portion oriented relative to the cover layer to receive the fluid conduit in a direction differing from another of the plurality of vacuum ports. The plurality of vacuum ports may include a pair of vacuum ports oriented such that a pair of conduit receiving portions may receive the fluid conduit in orthogonal directions. The wound dressing may further include at least one plug removably coupled to the conduit receiving portion of one of the plurality of vacuum ports. The plug may be configured to selectively form a substantially fluid-tight seal with the conduit receiving portion of the one of the plurality of vacuum ports.

The at least one vacuum port comprises a conduit receiving portion having a plurality of entry paths, each entry path oriented relative to the cover layer to receive the fluid conduit in a direction differing from another of the plurality of entry paths. The wound dressing may further include at least one plug removably coupled to one of the plurality of entry paths. The plug may be configured to form a substantially fluid-tight seal with the one of the plurality of entry paths. The at least one vacuum port may also include a flange extending radially from a central portion of the at least one vacuum port to facilitate the formation of a fluid-tight connection with the cover layer. The flange may comprise a plurality of vents formed therein.

The wound dressing may include a vacuum port having a base exhibiting a radial symmetry, and a conduit receiving portion that is selectively removable and selectively engaged by the base in a plurality of orientations. The conduit receiving portion may include an annular lip or notch, and the base may include an annular lip or notch such that the conduit receiving portion and the base are adapted for snap-fit engagement. The base may also include a socket mount configured to receive a bulbous end of the conduit receiving portion. The socket mount may be segmented to define a plurality of radially spaced slots on the base, and each of the slots may be configured to engage the conduit receiving portion to maintain an orientation of the conduit receiving portion. The bulbous end of the conduit receiving portion may include an o-ring for sealing a passageway through the base.

According to another aspect of the disclosure, a negative wound pressure therapy apparatus includes a cover layer for defining a reservoir over a wound in which a negative pressure may be maintained by forming a substantially fluid-tight seal around the wound. A vacuum source suitable for providing an appropriate negative pressure to the reservoir to stimulate healing of the wound and a fluid conduit in fluid communication with the vacuum source are provided. Also, the apparatus includes at least one vacuum port coupled to the cover layer and comprises a conduit receiving portion configured to receive the fluid conduit to provide fluid communication between the fluid conduit and the reservoir. The at least one vacuum port is configured to receive the fluid conduit from a plurality of directions relative to the cover layer. The apparatus may further include a contact layer in direct contact with the wound and a wound filler positioned between the contact layer and the cover layer.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

FIG. 5 through FIG. 7 are top views of various alternate embodiments of wound dressings for use with an NWPT apparatus;

DETAILED DESCRIPTION OF PREFERRED EMBODIMENTS

Figure 1:
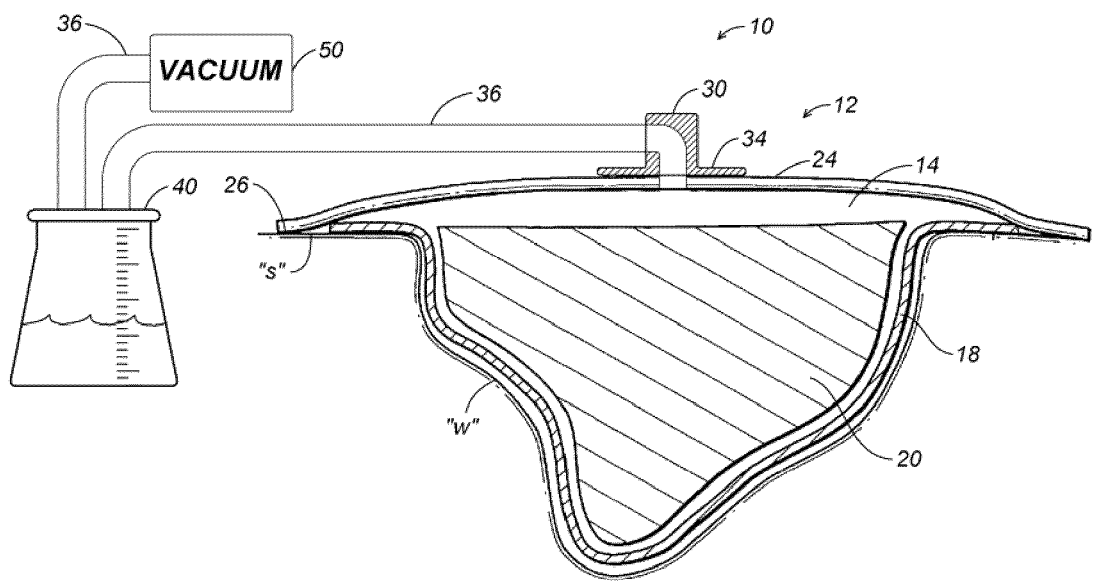
FIG. 1 is a cross sectional view of an NWPT apparatus having a wound dressing in accordance with the present disclosure.

The attached figures illustrate exemplary embodiments of the present disclosure and are referenced to describe the embodiments depicted therein. Hereinafter, the disclosure will be described in detail by explaining the figures wherein like reference numerals represent like parts throughout the several views.

Referring initially to FIG. 1, an NWPT apparatus is depicted generally as 10 for use on a wound "w" surrounded by healthy skin "s." The NWPT apparatus 10 includes a wound dressing 12 positioned relative to the wound "w" to define a reservoir 14 in which a negative pressure appropriate to stimulate healing may be maintained.

Wound dressing 12 includes a contact layer 18 positioned in direct contact with the bed of wound "w" and may be formed from perforated film material. An appropriate perforated material permits the negative pressure applied to the reservoir to penetrate into the wound "w," and also permits exudates to be drawn through the contact layer 18. Passage of wound fluid through the contact layer 18 is preferably unidirectional such that exudates do not flow back into the wound bed. Unidirectional flow may be encouraged by conical or directional apertures formed in the contact layer 18, or a lamination of materials having absorption properties differing from those of contact layer 18. A non-adherent material may be selected such that contact layer 18 does not tend to cling to the wound "w" or surrounding tissue when it is removed. One exemplary material that may be used as a contact layer 18 is sold under the trademark CURITY™ Non-Adhering Dressing by Kendall Corp., a division of Covidien.

Wound filler 20 is positioned in the wound "w" over the contact layer 18 and is intended to allow wound dressing 12 to transport wound exudates. Wound filler 20 can be cut to a shape that is conformable to the shape of wound "w," and may be packed up to the level of healthy skin "s," or alternatively, wound filler 20 may overfill the wound "w." A filler material such as gauze, reticulated foam, or alginate fibers may be used for filler 20 to receive or transport any exudate that migrates through contact layer 18. An antimicrobial dressing sold under the trademark KERLIX® AMD by Tyco Healthcare Group LP (d/b/a Covidien), may be suitable for use as filler 20.

Wound dressing 12 also includes a cover layer 24. Cover layer 24 may be positioned over the wound "w" such that an adhesive on an underside of the cover layer forms a substantially fluid-tight seal with the surrounding skin "s." Thus, cover layer 24 may act as both a microbial barrier to prevent contaminants from entering the wound "w," and also a fluid barrier maintaining the integrity of vacuum reservoir 14. Cover layer 24 is preferably formed from a moisture vapor permeable membrane to promote the exchange of oxygen and moisture between the wound "w" and the atmosphere, and is preferably transparent to permit a visual assessment of wound conditions without requiring removal of the cover layer 24. A transparent membrane providing a sufficient moisture vapor transmission rate (MVTR) for use as cover layer 24 is sold under the trade name POLYSKIN®II by Tyco Healthcare Group LP (d/b/a Covidien). Alternatively, cover layer 24 may comprise an impermeable membrane or a substantially rigid member.

A vacuum port 30 having a flange 34 is provided to facilitate connection of the wound dressing 12 to fluid conduit 36. An opening in the cover layer 24 that is smaller than the flange 34 may be provided to permit fluid communication between the reservoir 14 and the vacuum port 30. As described in greater detail below with reference to FIG. 3 through FIG. 10B, at least one vacuum port 30 may be coupled to cover layer 24 to permit a fluid conduit 36 to be routed according to the preference of the patient or caregiver. The vacuum port 30 may be configured as a rigid or flexible, low-profile component, and may be adapted to receive a fluid conduit 36 in a releasable and fluid-tight manner. An adhesive on the underside of flange 34 may provide a mechanism for affixing the vacuum port 30 to the dressing 12, or alternatively flange 34 may be positioned within reservoir 14 such that an adhesive on an upper side of the flange 34 affixes the vacuum port 30. Another alternative (not shown) involves placing the vacuum port 30 such that the underside of the flange 34 contacts the cover layer 24, and an additional membrane or skirt contacts the upper side of the flange. An adhesive on the skirt can adhere to the both the upper side of the flange and the cover layer 24 to hold the vacuum port 30 in place. However it is affixed to the dressing, a hollow interior of the vacuum port 30 provides fluid communication between the fluid conduit 36 and the reservoir 14. Vacuum port 30 may be provided as a pre-affixed component of dressing 12, as a component of fluid conduit 36 or entirely independently to be applied to the dressing 12 at the time of installation.

Fluid conduit 36 extends from the vacuum port 30 to provide fluid communication between the reservoir 14 and collection canister 40. Any suitable conduit may be used for fluid conduit 36 including those fabricated from flexible elastomeric or polymeric materials. Fluid conduit 36 may connect to the vacuum port 30, the canister 40, or other apparatus components by conventional air tight means such as friction fit, bayonet coupling, or barbed connectors. The conduit connections may be made permanent, or alternatively a quick-disconnect or other releasable means may be used to provide some adjustment flexibility to the apparatus 10.

Collection canister 40 may comprise any container suitable for containing wound fluids. For example, a rigid bottle may be used as shown or alternatively a flexible polymeric pouch may be appropriate. Collection canister 40 may contain an absorbent material to consolidate or contain the wound drainage or debris. For example, super absorbent polymers (SAP), silica gel, sodium polyacrylate, potassium polyacrylamide or related compounds may be provided within canister 40. At least a portion of canister 40 may be transparent to assist in evaluating the color, quality or quantity of wound exudates. A transparent canister may thus assist in determining the remaining capacity of the canister or when the canister should be replaced.

Leading from collection canister 40 is another section of fluid conduit 36 providing fluid communication with vacuum source 50. Vacuum source 50 generates or otherwise provides a negative pressure to the NWPT apparatus 10. Vacuum source 50 may comprise a peristaltic pump, a diaphragmatic pump or other mechanism that is biocompatible and draws fluids, e.g. atmospheric gasses and wound exudates, from the reservoir 14 appropriate to stimulate healing of the wound "w." Preferably, the vacuum source 50 is adapted to produce a sub-atmospheric pressure in the reservoir 14 ranging between about 20 mmHg and about 500 mmHg, more preferably, about 75 mmHg to about 125 mmHg, or more preferably between about 40 mmHg to about 80 mmHg.

Figure 2A:
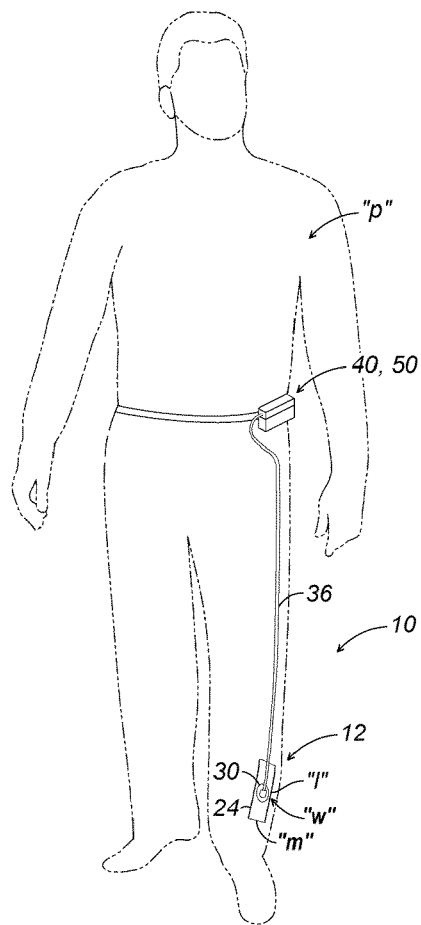
FIG. 2A is a schematic view of the NWPT apparatus of FIG. 1 in use on a patient.

Referring now to FIG. 2A, NWPT apparatus 10 is depicted schematically in use on a patient "p" with a wounded leg. Canister 40 and vacuum source 50 are depicted together as a portable unit worn on a belt to accommodate the mobility of the patient "p." Alternative embodiments of an NWPT apparatus may support canister 40 and vacuum source 50 elsewhere on the patient's body, or may include stationary external components for use with a bedridden patient. The particular position of the wound "w" in relation to the canister 40 and vacuum source 50 may determine a convenient route for fluid conduit 36. Preferably, fluid conduit 36 is routed close to the patient's body so as not to inhibit the patient's movement or comfort. Also a generally direct route between the wound "w" and the canister 40 is preferred.

Figure 2B:
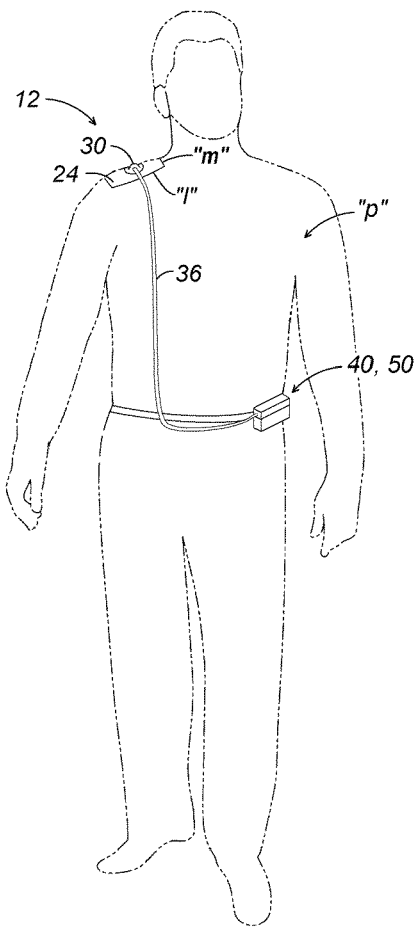
FIG. 2B is a schematic view of the NWPT apparatus in an alternate configuration.

The size, shape and location of the wound "w" may influence the manner in which fluid conduit 36 is routed relative to the wound dressing 12. For example, cover layer 24 assumes a generally rectangular shape with two longer sides "l" and two minor sides "m" to effectively cover the wound "w." Fluid conduit 36 extends from vacuum port 30 in a direction toward one of the minor sides "m" of the cover layer 24. Thus, flexible conduit 36 may continue up the patient's leg toward the canister 40 and vacuum source 50 without any unnecessary windings or flexures that could tend to kink the tubing. In other arrangements, such as the one depicted in FIG. 2B, it may be more convenient to route flexible conduit 36 such that it extends from vacuum port 30 in a direction toward one of the longer sides "l." Since the particular route most suitable for the flexible conduit 36 may not be known until the time the dressing 12 is applied, a dressing 12 may be configured to accommodate multiple arrangements.

Figure 3:
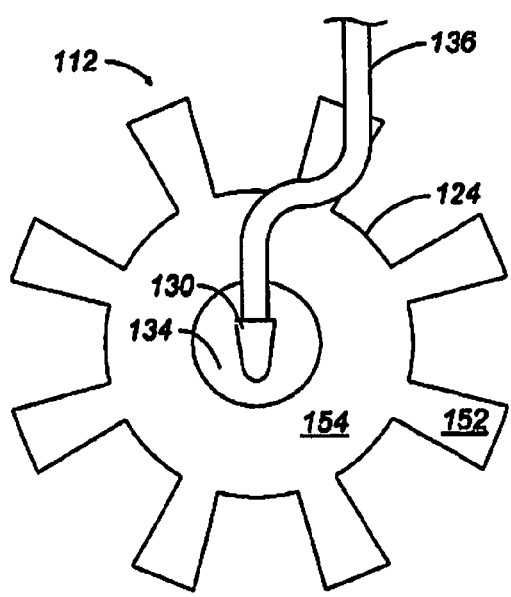
FIG. 3 is a top view of a wound dressing for use in an NWPT apparatus in accordance with the present disclosure.

Referring now to FIG. 3, a wound dressing in accordance with the present disclosure is depicted generally as 112. Wound dressing 112 includes a cover layer 124 adhesively coupled to a vacuum port 130. A flange 134 on the vacuum port 130 includes an adhesive on a lower surface to form a fluid-tight connection with the upper surface of cover layer 124, and the lower surface of the cover layer includes an adhesive to form a fluid-tight seal with the skin "s" of a patient "p" (see FIGS. 1 and 2A). Cover layer 124 is equipped with a plurality of limbs 152 extending radially outward from a central hub 154. Wound dressing 112 may be particularly useful for positioning over a wound "w" formed on a heel, elbow or other sharply contoured body part. Since a broad section of a polymeric film may not tend to conform readily to the skin "s" on a sharply contoured body part, a fluid tight seal may be established with the relatively smaller central hub 154, while the limbs 152 extend further outward to provide support to maintain the position of the dressing 112. This arrangement may tend to reduce the likelihood of wrinkles and folds that could compromise the formation of a fluid-tight seal.

Wound dressing 112 exhibits a symmetry that permits fluid conduit 136 to extend from vacuum port 130 in a proper direction. The dressing 112 may be placed over the wound "w" in the orientation most suitable for routing the fluid conduit 136 with little or no impact on the relative positioning of the limbs 152. When the size, shape or position of a wound "w" does not allow for this symmetry, another type of conduit connection may be necessary.

Figure 4A:
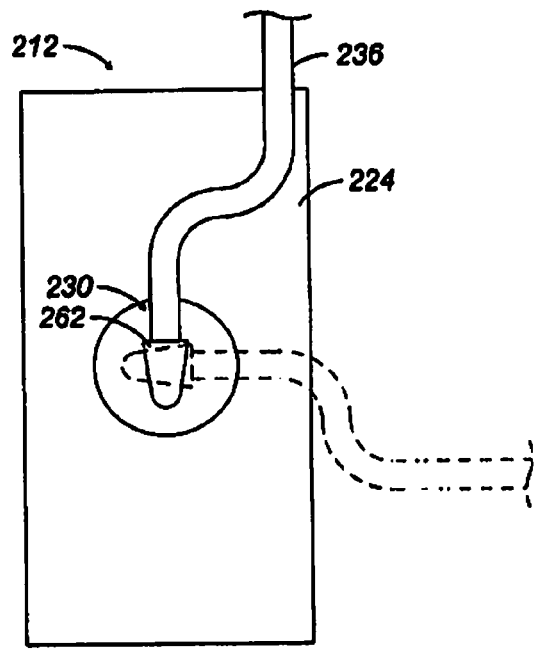
FIG. 4A is a top view of an alternate embodiment of a wound dressing.

Referring now to FIG. 4A, a non-symmetrical wound dressing 212 includes a cover layer 224 coupled to a vacuum port 230. Vacuum port 230 receives fluid conduit 236 in a conduit receiving portion 262 configured to rotate relative to the cover layer 224. Thus, fluid conduit 236 may be readily routed regardless of the orientation and positioning of the dressing 212.

Figure 4B:
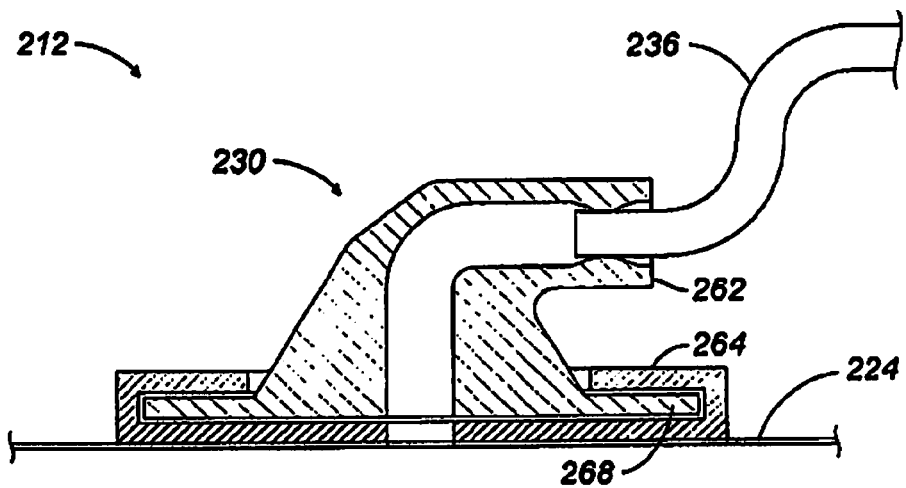
FIG. 4B is a cross-sectional view of the wound dressing of FIG. 4A.

As depicted in FIG. 4B, vacuum port 230 includes a base 264, which is adhesively coupled to the cover layer 224. The conduit receiving portion 262, for receiving fluid conduit 236, includes a lower flange 268 that is captured by the base 264 such that the conduit receiving portion 262 may rotate within the base 264. Since the base remains stationary relative to the cover layer 224, conduit receiving portion 262 rotates relative to the cover layer 224. An o-ring or similar fluid tight seal (not shown) may be incorporated into vacuum port 230 to ensure atmospheric gasses do not flow between the base and the conduit receiving portion 262.

Preferably, conduit receiving portion 262 may rotate at least 360 degrees in either direction. Vacuum port 230 may be configured such that conduit receiving portion 262 rotates through its range of motion freely, or alternatively vacuum port 230 may incorporate an orientation fixation structure (not shown) to releasably lock conduit receiving portion 262 in position relative to the base 264. For example, either the conduit receiving portion 262 or the base 264 may be equipped with a series of spaced ridges or detents arranged along a path corresponding to the range of motion of the conduit receiving portion. The other of the conduit receiving portion 262 and the base 264 may be equipped with a flexible pawl to interface with the spaced ridges or detents in a ratchet-like manner. Thus, conduit receiving portion 262 may tend to remain in position until purposely acted upon to rotate.

Referring now to FIG. 5 an alternate embodiment of a wound dressing is depicted generally as 312. Wound dressing 312 includes a cover layer 324 coupled to a plurality of vacuum ports 330. Each vacuum port 330 is oriented such that fluid conduit 336 may be received in a conduit receiving portion 362 from a different direction. A user may thus select the vacuum port most suitable for routing the fluid conduit 336. A plug 366 may be provided for each non-selected vacuum ports 330 to maintain a fluid-tight seal. Plug 366 may be removably coupled to the conduit receiving portion of each of the non-selected vacuum ports and may form a substantially fluid-tight seal therewith. As depicted in FIG. 5, two vacuum ports 330 are oriented such that the conduit receiving portions may receive the fluid conduit from orthogonal directions. However, any number of vacuum ports 330 may be included and each may be oriented in any direction relative to the cover layer 324.

Referring now to FIG. 6, another alternate embodiment of a wound dressing is depicted generally as 412. Wound dressing 412 includes a cover layer 424 coupled to a vacuum port 430, which is configured to receive fluid conduit 436 from a plurality of directions. Vacuum port 430 includes a conduit receiving portion 462 having a plurality of entry paths for the fluid conduit 436. A user may thus select the entry path most suitable for routing the fluid conduit 436. A plug 466 may be provided for each non-selected entry path to maintain a fluid-tight seal. As depicted in FIG. 6, two entry paths are oriented in orthogonal directions. However, any number of entry paths may be included and each may be oriented in any direction relative to the cover layer 424.

Referring now to FIG. 7, another alternate embodiment of a wound dressing is depicted generally as 512. Wound dressing 512 includes a cover layer 524 coupled to a vacuum port 530. Vacuum port 530 includes a conduit receiving portion 562, which may be configured to receive fluid conduit 536 from a plurality of directions in a manner similar to vacuum port 230 (FIG. 4A). Alternatively vacuum port 530 may accommodate only a single direction (not shown) for use in a wound dressing similar to wound dressing 312 (FIG. 5). Vacuum port 530 includes a flange 568 extending radially outward from a central portion of the vacuum port to facilitate the formation of a fluid-tight connection with the cover layer 524.

A plurality of circular vents 570 extend through the flange 568 and provide a pathway for moisture vapor transmission. The vents 570 allow for flange 568 to cover a larger area of the cover layer 524 with less impact on the MVTR associated with the dressing 512. A relatively larger flange 568 may be capable of providing a more secure seal with the cover layer 524 and thus enhance the effectiveness of an NWPT treatment. Additionally, vents 570 provide a degree of flexibility to the flange 568 that allows the flange 568 to conform to the particular contours of a body part. This flexibility promotes patient comfort.

Figure 8A:
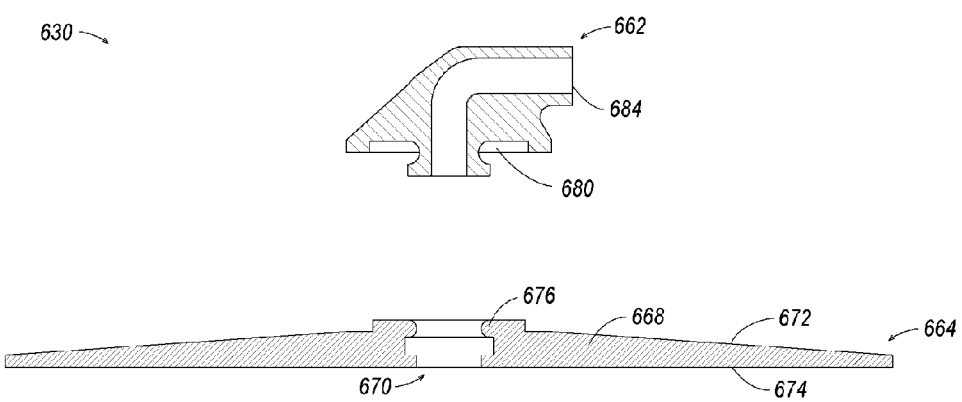
FIG. 8A is an exploded cross-sectional view of an embodiment of a vacuum port in accordance with the present disclosure.

Referring now to FIG. 8A, a two-component vacuum port is depicted generally as 630. Vacuum port 630 includes a conduit receiving portion 662 and a separable base 664. The base 664 exhibits a radial symmetry that allows it to be connected to a cover layer (now shown) before a preferred orientation is determined. The conduit receiving portion 662 may be attached to the base 664 in any orientation once a convenient route for a fluid conduit is established.

Figure 8B:
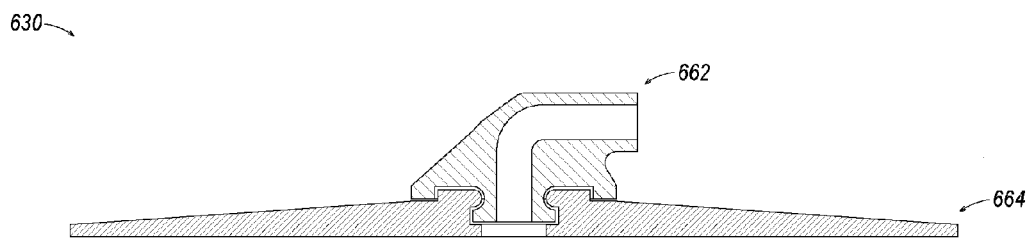
FIG. 8B is an assembled cross-sectional view of the vacuum port of FIG. 8A.

The base 664 includes a flange 668 extending radially outward from a central passageway 670. The flange 688 provides broad upper and lower adhesion surfaces, 672 and 674 respectively, to facilitate connection with a cover layer. The passageway 670 provides fluid communication through the base 664 and also receives the conduit receiving portion 662. An annular lip 676 extending into the passageway 670 provides an interface for an annular notch 680 on the conduit receiving portion 662. Both the annular lip 676 and the annular notch 680 exhibit radial symmetry such that a conduit interface 684 may be oriented in any radial direction with respect to the base 664. As depicted in FIG. 8B, the conduit receiving portion 662 and the base 664 may be engaged by a snap-fit connection in fixed relation to one another. Adjustments to the orientation of the conduit interface 684 may be made by disconnecting the conduit receiving portion 662 from the base, and reattaching to the two components in the desired orientation.

Figure 9A:
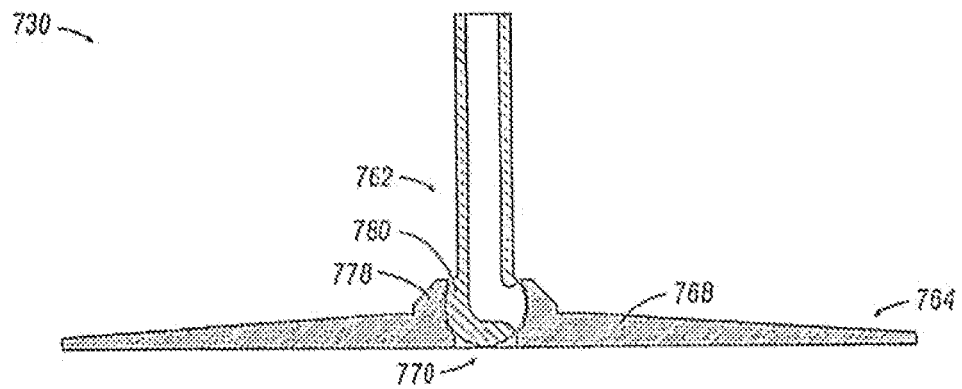
FIG. 9A is a cross-sectional view of an alternate embodiment of a vacuum port.

Referring now to FIG. 9A, an alternate embodiment of a two-component vacuum port is depicted generally as 730. Vacuum port 730 includes a conduit receiving portion 762 and a base 764 that accepts the conduit receiving portion 762 in a plurality of orientations. The base 764 includes a flange 768 extending radially outward from a passageway 770. A socket mount 778 encircles the passageway 770 to receive a bulbous end 780 of the conduit receiving portion 762 to establish a ball and socket joint. The conduit receiving portion 762 may be snap-fit into the socket mount 778 in an upright orientation, where it is freely rotatable in any direction, and thereafter rotated downward to establish fluid communication between the passageway 770 and an interior 788 of the conduit receiving portion 762.

Figure 9B:
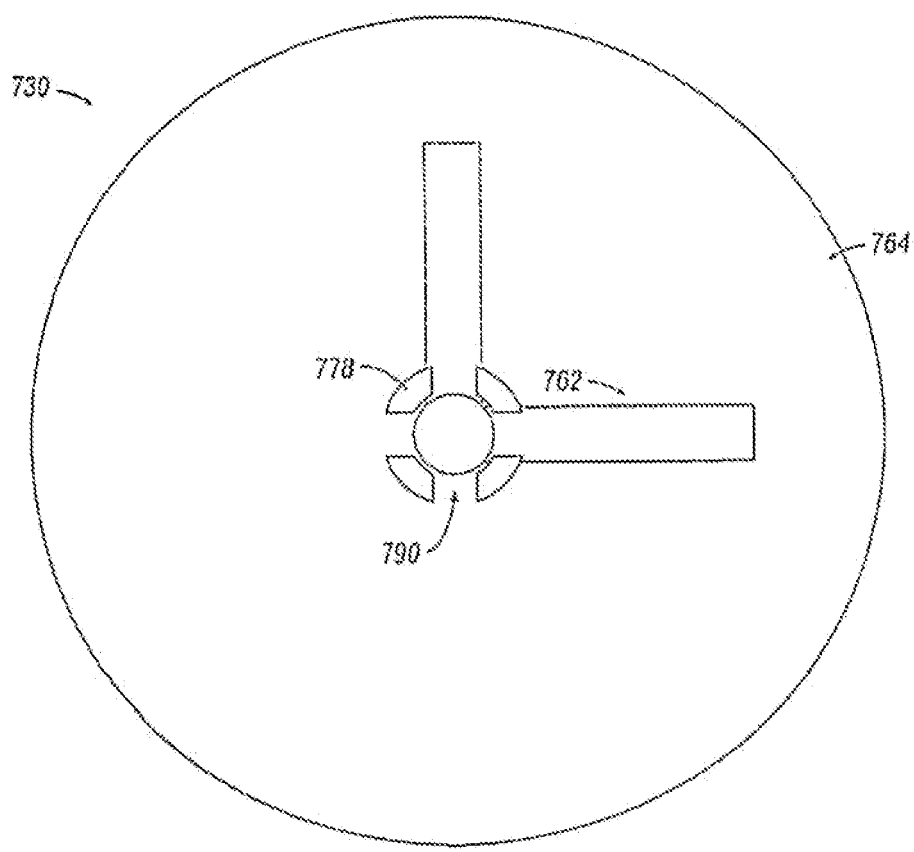
FIG. 9B is a top view of the vacuum port of FIG. 9A.

As depicted in FIG. 9B, the socket mount 778 is segmented such that the conduit receiving portion may be rotated downward into one of four radially spaced slots 790. The slots 790 may be configured to engage the conduit receiving portion 762 in a snap-fit manner to lock the vacuum port 730 in the selected orientation. Adjustments to the orientation of the conduit receiving portion 762 may be made by rotating conduit receiving portion 762 upwards into the freely rotatable orientation, and then back down into an alternate slot as depicted in phantom. FIG. 9B depicts four slots 790 allowing for 90 degree adjustments, but any number of slots is contemplated.

Figure 10A:
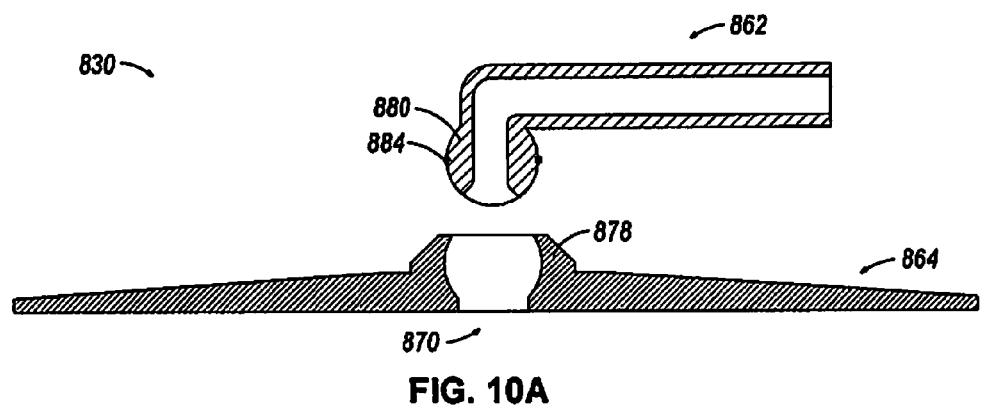
FIG. 10A is an exploded cross-sectional view of another alternate embodiment of a vacuum port.
Figure 10B:
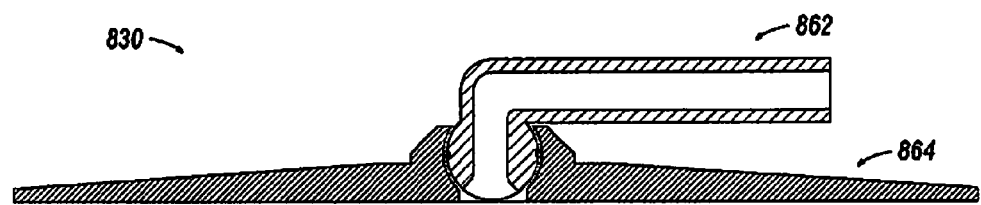
FIG. 10B is an assembled cross-sectional view of the vacuum port of FIG. 10A.

Referring now to FIG. 10A, another alternate embodiment of a two-component vacuum port is depicted generally as 830. Vacuum port 830 includes a conduit receiving portion 862 and a base 864 that accepts the conduit receiving portion 862 in a rotatable manner. A passageway 870 through the base 864 is encircled by a socket mount 878. The socket mount 878 is continuous to receive a bulbous end 880 of the conduit receiving portion 862 in any radial orientation. Bulbous end 880 includes an o-ring 884 or similar seal molded thereto. O-ring 884 engages the socket mount 878 when the conduit receiving portion 862 is engaged by the base 864 as depicted in FIG. 10B. O-ring 884 seals the passageway 870 and provides a frictional contact therewith to maintain the orientation of the conduit receiving portion 862. Adjustments to the orientation of the conduit receiving portion 862 may be made simply by overcoming this frictional contact.

Figure 11:
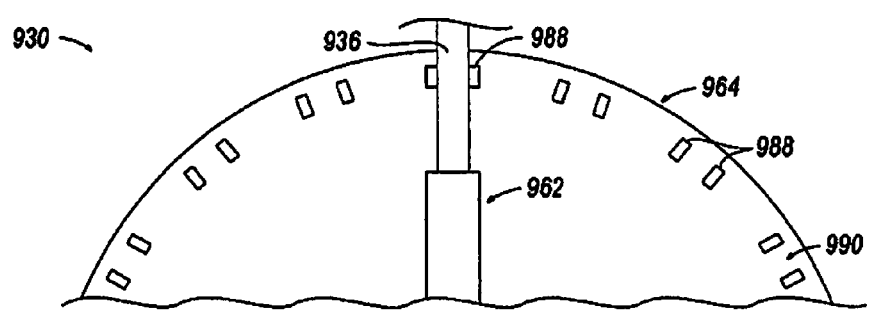
FIG. 11 is a partial top view of another alternate embodiment of a vacuum port.

Referring now to FIG. 11, another alternate embodiment of a two-component vacuum port is depicted generally as 930. A fluid conduit 936 is received in a conduit receiving portion 962 that is configured for rotation relative to a base 964. The conduit receiving portion 962 may engage the base 964 with a lower flange as described above with reference to FIG. 4B, by a ball and socket arrangement as described above with reference to FIG. 10B, or by another suitable mechanism. Base 964 extends radially outward beyond conduit receiving portion 962 where it supports a plurality of projections 988. The projections 988 extend a sufficient distance from the base 964 such that each of a plurality of slots 990 defined between the projections 988 may receive the fluid conduit 936. The slots 990 may receive the conduit 936 in a friction-fit or a snap-fit manner to fix the orientation of the conduit 936.

Although the foregoing disclosure has been described in some detail by way of illustration and example, for purposes of clarity or understanding, it will be obvious that certain changes and modifications may be practiced within the scope of the appended claims.

What is claimed is:

1. A wound dressing for use in negative wound pressure therapy comprising:
   a cover layer for positioning over a wound to define a reservoir over the wound in which a reduced pressure may be maintained; and
   at least one vacuum port configurable into a plurality of discrete predefined orientations, the at least one vacuum port comprising:
   a stationary base affixed to the cover layer;
   a conduit receiving portion configured to provide fluid communication between a fluid conduit and the reservoir, the conduit receiving portion adapted for rotational movement relative to the stationary base into any of the plurality of predefined orientations;
   an orientation fixation structure configured to lock the conduit receiving portion in position relative to the stationary base in a releasable manner, wherein the orientation fixation structure comprises a pawl on one of the stationary base and the conduit receiving portion, the pawl configured to interface with a series of space ridges or detents on the other of the stationary base and the conduit receiving portion in a ratchet-like manner.

2. The wound dressing according to claim 1, wherein the orientation fixation structure comprises a plurality of radially spaced projections extending from the stationary base radially beyond the conduit receiving portion to define a plurality of radially spaced slots therebetween, the slots configured to receive the fluid conduit.

3. The wound dressing according to claim 1, wherein the at least one vacuum port comprises a plurality of vacuum ports, each of the plurality of vacuum ports having a conduit receiving portion oriented relative to the cover layer to receive the fluid conduit in a direction differing from another of the plurality of vacuum ports.

4. The wound dressing according to claim 3, wherein the plurality of vacuum ports includes a pair of vacuum ports oriented such that respective conduit receiving portions thereof are orthogonally oriented.

5. The wound dressing according to claim 3, further comprising at least one plug removably coupled to the conduit receiving portion of one of the plurality of vacuum ports, the plug configured to form a substantially fluid-tight seal with the conduit receiving portion of the one of the plurality of vacuum ports.

6. The wound dressing according to claim 1, wherein the conduit receiving portion is configurable into the plurality of discrete predefined orientations each corresponding to a plurality of entry paths.

7. The wound dressing according to claim 6, further comprising at least one plug removably coupled to one of the plurality of entry paths, the plug configured to form a substantially fluid-tight seal with the one of the plurality of entry paths.

8. The wound dressing according to claim 1, wherein the at least one vacuum port comprises a flange-affixing the at least one vacuum port to the cover layer.

9. The wound dressing according to claim 8, wherein the flange of the at least one vacuum port comprises a plurality of vents formed therein.

10. The wound dressing according to claim 1, wherein the stationary base of the at least one vacuum port exhibits a radial symmetry, and wherein the conduit receiving portion of the at least one vacuum port is selectively removable and selectively engagable with the stationary base into the plurality of discrete predefined orientations.

11. The wound dressing according to claim 10, wherein the conduit receiving portion includes an annular lip or notch, and wherein the stationary base includes an annular lip or notch such that the conduit receiving portion and the stationary base are adapted for snap-fit engagement.

12. The wound dressing according to claim 10, wherein the base includes a socket mount configured to receive a bulbous end of the conduit receiving portion.

13. The wound dressing according to claim 12, wherein the socket mount is segmented to define a plurality of radially spaced slots on the base, each of the slots being configured to engage the conduit receiving portion to maintain an orientation of the conduit receiving portion.

14. The wound dressing according to claim 12, wherein the conduit receiving portion includes an o-ring for sealing a passageway through the base.

15. A negative wound pressure therapy apparatus comprising:
   a cover layer for defining a reservoir over a wound in which a negative pressure may be maintained by forming a substantially fluid-tight seal around the wound;
   a vacuum source suitable for providing an appropriate negative pressure to the reservoir;
   a fluid conduit in fluid communication with the vacuum source; and
   at least one vacuum port configured to selectively receive the fluid conduit from anyone of a plurality of discrete predefined directions, the at least one vacuum port comprising;
   a stationary base affixed to the cover layer;
   a conduit receiving portion configured to receive the fluid conduit to provide fluid communication between the fluid conduit and the reservoir, the conduit receiving portion adapted for rotational movement relative to the stationary base into any of the plurality of predefined directions; and
   an orientation fixation structure configured to lock the conduit receiving portion in position relative to the stationary base in a releasable manner, wherein the orientation fixation structure comprises a pawl on one of the stationary base and the conduit receiving portion, the pawl configured to interface with a series of space ridges or detents on the other of the stationary base and the conduit receiving portion in a ratchet-like manner.

16. The apparatus according to claim 15, further comprising a contact layer in direct contact with the wound and a wound filler positioned between the contact layer and the cover layer.

* * * * *